United States Patent [19]

Fujimori et al.

[11] 4,430,896
[45] Feb. 14, 1984

[54] METHOD AND APPARATUS FOR DETECTING CRACK PRODUCED IN WORKPIECE IN DISTORTION REMOVAL PROCESSING

[75] Inventors: Kazuo Fujimori; Akira Banno, both of Toyota, Japan

[73] Assignee: Toyota Jidosha Kogyo Kabushiki Kaisha, Toyota, Japan

[21] Appl. No.: 361,252

[22] Filed: Mar. 24, 1982

[51] Int. Cl.$^3$ .............................................. G01N 29/04
[52] U.S. Cl. .................................... 73/587; 73/660; 73/801
[58] Field of Search ........................... 73/587, 801, 660

[56] References Cited

U.S. PATENT DOCUMENTS 4,036,057  7/1977  Morais .................................. 73/801
4,344,326  8/1982  Kahn ..................................... 73/801

OTHER PUBLICATIONS

"Utilization of Acoustic Emission for In-Service Inspection", Schofield, *Conference on Periodic Inspection of Pressure Vessels*, London, England, Institution of Mech. Engineers, May 9-11, 1972, Paper No. S3045 0056, pp. 76-82.

"Acoustic Emission System for Monitoring Components and Structures in a Severe Fatigue Noise Environment," Horak et al., *Materials Evaluation*, May 1977, pp. 59-63.

*Primary Examiner*—Howard A. Birmiel
*Attorney, Agent, or Firm*—Cushman, Darby & Cushman

[57] ABSTRACT

An apparatus for detecting cracks possibly produced in a workpiece whose distortion is being removed under pressure exerted by a pressing rod of a distortion removing machine. A detection signal produced by a sensor embedded in the pressing rod during a first predetermined period is compared with a first predetermined signal level for determining whether or not the cracking occurs in the workpiece. A detection signal produced by the acoustic emission sensor during a second predetermined period in which the workpiece is subjected to the pressure of the pressing rod without involving cracks is compared with a second predetermined signal level to determine whether or not the detecting apparatus itself operates normally.

5 Claims, 6 Drawing Figures

METHOD AND APPARATUS FOR DETECTING CRACK PRODUCED IN WORKPIECE IN DISTORTION REMOVAL PROCESSING

The present invention relates generally to a method and apparatus for detecting occurrence of cracks in a workpiece such as a shaft when the workpiece is processed in a distortion removing machine. More particularly, the present invention concerns a method and apparatus which are capable of instantaneously detecting with an enhanced reliability the cracks possibly produced in the workpiece in processing for removing distortion thereof on the basis of detection of acoustic emission signals emitted by the workpiece which is undergoing the distortion removal processing.

Among workpieces such as shafts and the like for use as components of motor vehicles, some are subjected to a thermal processing such as a high frequency surface cementation hardening, for example. As the result, the workpiece undergoing the thermal processing is susceptible to distortion such as bending, which involves serious problems in particular when the workpiece is a rotating member such as a shaft. In fact, distortion of the shaft inevitably gives rise to non-uniform rotation of the shaft and additionally makes it very difficult to mount the shaft with a required precision. For this reason, the workpieces undergoing thermal distortion are usually subjected to subsequent processing for removing the distortion.

In the distortion eliminating process, there may possibly occur cracks in the workpiece in dependence on magnitude of distortion, pressure load applied to the workpiece and variation in load. Under the circumstances, the workpiece undergoing the distortion eliminating process is usually inspected as to the presence of the cracks by using a pulverized magnetic material. However, the inspection which resorts to the use of pulverized magnetic material for detecting the defects takes a lot of time and is disadvantageous in that the result of detection tends to be indefinite in dependence on concentration of the magnetic powder as used. In this conjunction, there has been known a method of detecting the crack by making use of an acoustic emission signal produced by a workpiece to be examined in various tests such as, for example, tensioning test, bending test, fatigue test for determining yield points. However, an automatic method of detecting cracks produced in materials to be worked or in workpieces in site on a production line is not yet practiced. This can be ascribed to the fact that noises produced by vibrations of various machine parts renders it very difficult to detect with reliability the acoustic emission signal emitted due to occurrence of cracks in the workpiece being processed, and that determination as to whether a measuring or detecting system for detecting the acoustic emission signal is normally operating or not can not be effected in a reliable and facilitated manner.

An object of the present invention is accordingly to provide a method and an apparatus which are capable of detecting the cracks possibly produced in a workpiece being processed for removing distortion thereof on the bais of an acoustic emission signal produced by the workpiece and detectd at a high S/N ratio.

In view of the above and other objects which will become more apparent as the description proceeds, it is proposed according to a feature of the invention that an acoustic emission signal sensor is embedded in a pressing rod or a support table of a distortion removing machine. Further, a first period in which an acoustic emission signal may possibly be emitted due to occurrence of cracks in the workpiece being processed for removing distortion is set, while a second period in which acoustic emission signal due to other causes than cracks is produced is established. The acoustic emission signal produced during the first period from the output of the sensor embedded in the pressing rod or work table of the distortion removing machine is compared with a first predetermined signal level to thereby determine the occurrence or non-occurrence of cracks, while the acoustic emission signal produced during the second period is compared with a second predetermined signal level to thereby determine whether the detecting apparatus itself is operating properly or not.

According to the invention, detection of occurrence of the cracks can be effected with an enhanced reliability in a very inexpensive and simple hardware structure on a real time base without involving troublesome and time-consuming procedures such as magnetization, distribution of magnetic powder and the like required in the hitherto known magnetic particle testing method. Further, the invention allows the crack detecting process as well as the distortion removing process to be carried out in an automated manner within a remarkably shortened time.

Further, since the crack detecting operation is effectd only during the period in which the cracks are expected to be produced in the distortion removing process, the occurrence of the cracks can be detected with a high accuracy and reliability. The sensor embedded in the pressing rod or supporting table of the distortion removing machine can receive the acoustic emission signals in a stabilized manner. Further, because the operation of the crack detecting apparatus is necessarily tested or checked once in every distortion removing process, the result of the crack detection can assure a high fidelity. Moreover, there is no necessity of providing a specific circuit for performing the check mentioned above, resulting in simplification in the configuration of circuits as used.

The above and other objects, features and advantages of the invention will be more apparent from description of a preferred, but non-limiting embodiment of the invention. The description makes reference to the accompanying drawings, in which.

In the following, the invention will be described in more detail in conjunction with a preferred embodiment thereof shown in the accompanying drawings.

Figure 1A:
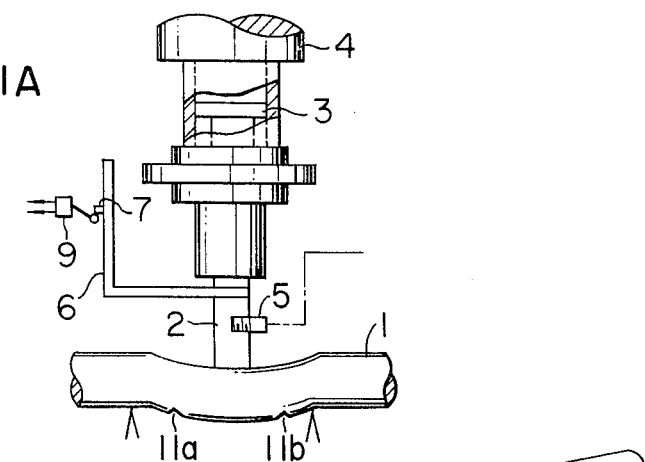
FIG. 1A shows in a schematic front view a mechanical portion of a crack detecting apparatus according to an exemplary embodiment of the invention.

Referring to FIG. 1A, there is shown schematically a mechanical portion, i.e. a distortion removing machine provided with peripheral devices to which a crack detecting apparatus accordin to the invention can be applied. In this figure, a reference numeral 1 denotes a workpiece which is subjected to a pressure for removing distrotion thereof, 2 denotes a pressed rod, 3 denotes a piston connected operatively to the pressing rod 2, and a numeral 4 designates a hydraulic cylinder for displacing the pressing rod 2 upwardly and downwardly by way of the piston 3. A sensor 5 for detecting an acoustic emission signal is embedded in the pressing rod 2. Further, an L-like arm member 6 is fixedly mounted on the pressing rod 2 and has an upstanding leg portion provided with a projection 7 at a predetermined position so that the projection 7 is brought into contact with a actuator lever of a limit switch 9 when the pressing rod 2 is moved upwardly or downwardly. More specifically, the lever of the limit switch 9 and the projection 7 are disposed at such relative positions that the limit switch 9 is closed or turned on by the projection 7 when the pressing rod 2 which is initiated to move downwardly from an upper predetermined position comes to contact with the workpiece 1, while the limit switch 9 is opened or turned off by means of the projection 7 when the pressing rod 2 is moved upwardly to the position at which the pressing rod 2 was first brought into contact with the workpiece 1 in the course of the downward stroke thereof.

Figure 1B:
FIG. 1B illustrates typical patterns of acoustic emission signals detected by a sensor in a distortion removing process.

FIG. 1B graphically illustrates typical examples of acoustic emission signals which can be detected by the sensor 5 according to the invention in the processing of a workpiece to remove distortion thereof. Referring to FIG. 1A, a waveform illustrated at (a) corresponds to the acoustic emission signal detected when no cracks are produced. On the other hand, a waveform illustrated at (b) corresponds to the cracking acoustic emission signal radiated upon occurrence of cracks $11a$ and $11b$ (refer to FIG. 1) when the workpiece 1 is subjected to a pressure of the pressing rod 2.

Figure 2:
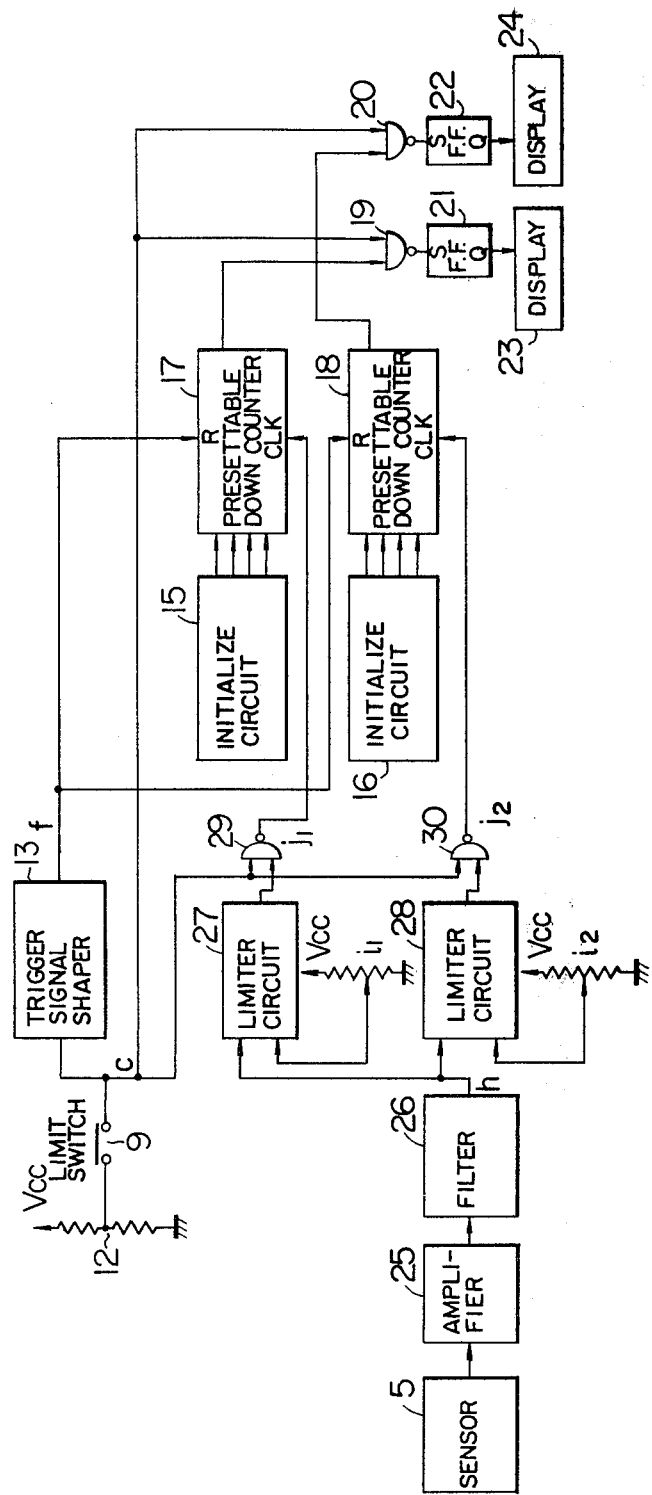
FIG. 2 shows in a circuit diagram an electric circuit portion of the crack detecting apparatus according to an exemplary embodiment of the invention.
Figure 3:
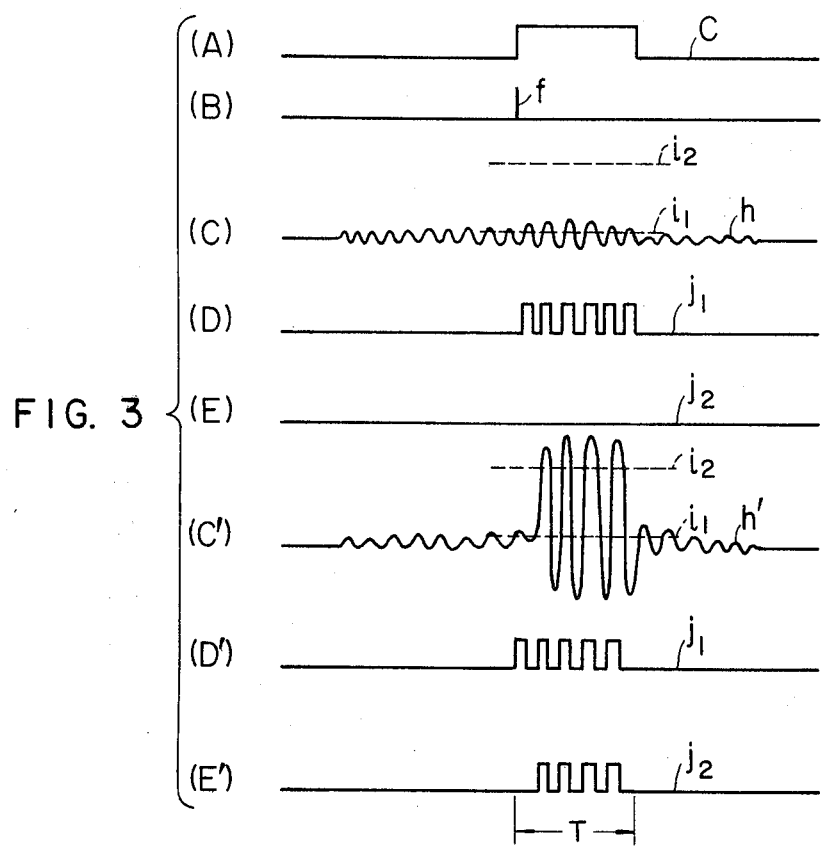
FIG. 3 shows waveforms of signals produced at various circuit points of the electric circuit shown in FIG. 2 for illustrating operations of the circuit.

FIG. 2 shows in a circuit diagram an electric system, i.e. a crack detecting circuit according to an exemplary embodiment of the present invention, and FIG. 3 illustrates waveforms of signals produced at various circuit points of the crack detecting circuit shown in FIG. 2. Referring to FIG. 2, the reference numerals 5 and 9 designate, respectively, the sensor and the limit switch described above in conjunction with FIG. 1A. The limit switch 9 has one end connected to a voltage divider resistor 12 which serves to derive a predetermined voltage from a source voltage. Since the limit switch 9 is held in the closed or turned-on state during a period which begins at a time point when the lower end face of the pressing rod 2 is first brought into contact with the workpiece 1 in the course of the downward stroke thereof and ends at a time point when the lower end of the pressing rod 2 again comes to the position at which it was first contacted with the workpiec 1 in the course of the upward movement after completion of the distortion removal processing, there appears at the other end of the limit switch 9 a signal c of a waveform shown in FIG. 3 at (A). This period during which the signal c takes the predetermined voltage level represented by logic "1" corresponds to a period of a length T during which the acoustic emission signal illustrated in FIG. 1B may be produced due to possible occurrence of cracks. This period the length T is also referred to as the period I. In this connection, it will be appreciated that although the period I of the duration T is set by means of the limit switch 9 in the case of the illustrated embodiment, any other suitable means such as a touch sensor switch or pressure switch may be employed to this end so far as the logic "1" level of the signal c can be discriminatively produced. Further, although description is made on the assumption that the period I during which the acoustic emission signal may be produced due to possible occurrence of cracks in the workpiece is set in coincidence with a period II during which acoustic emission signal ascribable to other causes than the cracking of the workpiece is produced, it is of course possible to set the periods I and II discriminatively from each other. For example, two limit switches are used for this purpose. Referring to FIG. 2, numerals 17 and 18 denote, respectively, presettable down-counters whose initial values are supplied from initial value setting circuits or initializing circuits 15 and 16, respectively. A trigger signal shaping circuit 13 is adapted to produce a trigger signal f in response to a rise-up edge of the period defining signal c. Reference is to be made to FIG. 3 at (B). The downcounters 17 and 18 are reset by the trigger signal f. These down-counters 17 and 18 count pulses supplied as clock pulses from limiter circuits 27 and 28 through NAND circuits 29 and 30, respectively. When the initially set values have been counted down to zero, the down-counters 17 and 18 supply signals to set inputs of flip-flops 21 and 22 through NAND gates 19 and 20, respectively. The outputs from the flip-flops 21 and 22 are supplied, respectively, to display means 23 and 24 for activation thereof.

Next, description will be made on the operation or function of the acoustic emission signal detector circuit shown in FIG. 2. When a single cycle of the distortion removal processing is executed in the manner described hereinbefore, the acoustic emission signal shown in FIG. 1B at (a) or (b) is detected by the sensor 5. For convenience of elucidation, the output waveform of the sensor 5 is illustrated in FIG. 3 at (c) in a simplified form. The detection signal h which represents the output signal from the sensor 5 after having been conditioned to an appropriate level through an amplifier circuit 25 and a filter circuit 26 is shaped into pulse signals $j_1$ and $j_2$ with reference to predetermined standard or threshold levels $i_1$ and $i_2$, as illustrated at (c) in FIG. 3. These pulse signals $j_1$ and $j_2$ shown in FIG. 3 at (D) and (E) are supplied as the count or clock pulses to the downcounters 17 and 18 through the NAND circuits 29 and 30, respectively, which are enabled during the period in which the signal c is at the logic "1" level. In other words, the pulse signals $j_1$ and $j_2$ are supplied to the downcounters 17 and 18, respectively, during the period of duration T in which cracking of the workpiece may possibly occur.

In the first place, description will be made of the operation on the assumption that no cracking takes place in the distortion removal processing. In this case, the detection signal h is of such a waveform as shown in FIG. 3 at (c). The reference level signals $i_1$ and $i_2$ applied to the inputs of the limiter circuits 27 and 28, respectively, are so set that $i_1 \ll i_2$. So far as no cracking occurs, the detection signal h has an amplitude which exceeds the reference or standard level $i_1$ but does not attain the other reference level $i_2$. As a consequence, the detection signal h is shaped into the corresponding pulse signal through the only limiter circuit 27 that is applied with the reference or threshold level $i_1$ at the input thereof. The pulse signal $j_1$ thus produced from the limiter circuit 27 is transmitted to the downcounter 17 through the NAND circuit 29 which is enabled during the period T in which the signal c is at the logic "1" level. The down-counter 17 has been reset in response to the rise-up edge of the signal c and previously loaded with an initial value representative of non-occurrence of cracking. When the number of the pulses $j_1$ counted by the down-counter 17 exceeds the initial value, the flip-flop 21 is set through the NAND circuit 19 to activate the display means 23 and maintain it in the activated state. The initial value set at the down-counter 17 is selected sufficiently smaller than the number of pulses $j_1$ derived from the acoustic emission signal when no crack is produced.

Next, it is assumed that cracks are produced in the workpiece in the course of the processing for removing distortion. The detection signal designated by h' then has an amplitude which is significantly higher than that of the detection signal h produced when no crack occurs and exceeds the reference level $i_2$ (refer to FIG. 3 at C). Thus, the detection signal h' is shaped into pulse signals $j_1$ and $j_2$ through both the limiter circuits 27 and 28. Since the NAND circuits 29 and 30 are enabled during the period in which the signal c remains logic "1", the pulse signal $j_1$ is supplied to the down-counter 17 with the pulse signal $j_2$ being supplied to the other down-counter 18. The down-counter 17 is previously loaded with the initial value representative of the non-occurrence of a crack in response to the rise-up edge of the signal c, while the down-counter 18 is set at the initial value representative of the occurrence of a crack in response to the rise-up edge of the signal c. Under the circumstances, both of the pulse signals $j_1$ and $j_2$ counted by both the down-counters 17 and 18 exceed the respective initial values, whereby the assocated flip-flop 21 and 22 are set through the AND circuits 19 and 20 to activate the display means 23 and 24 and maintain them in the activated state. In this connection, it is to be noted that the initial value set by the initializing circuit 16 is selected smaller than the number of pulses $j_2$ which can be derived from the acoustic emission signal produced when cracking occurs.

In this way, when the display means 24 is activated in addition to the display means 23, an operator can determine that cracking occurs in the workpiece being processed. On the other hand, when only the display means 23 is activated with the other display means 24 remaining deenergized, it is determined that no crack is produced. Further, unless the display means 23 is activated at all, then it is expected that a fault occurs in the crack detecting apparatus. By the way, one or both outputs from the flip-flops 21 and 22 may be additionally utilized for stopping operation of the processing machine and other purposes.

Next, an exemplary structure for mounting the sensor 5 will be described by referring to FIG. 4A which shows in a fragmental enlarged view a mounting structure of the sensor 5. For detecting the acoustic emission signal with a high stability and reliability, it is important that deposition of ducts or the like foreign particles on the sensitive surface of the sensor should be positively excluded. To this end, a hole is formed in the pressing rod 2 and the sensor 5 is inserted in the hole together with an O-ring seal 35 for preventing dusts or the like foreign particles from entering the hole and being deposited on the pressure sensitive face 38 of the sensor 5. Further, a spring 36 supported by means of a sensor holder 37 serves to support the sensor 5 under a constant pressure. It is thus assured that the acoustic emission signal is detected with a high stability for a long period.

Figure 4B:
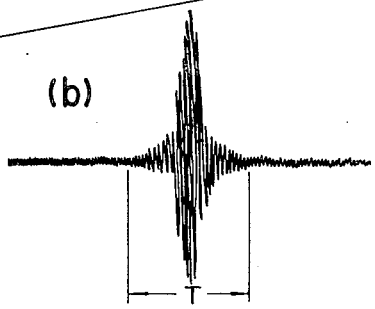
FIG. 4A and 4B illustrate schematically mounting structures of the sensor in fragmental sectional front views.
Figure 4B:
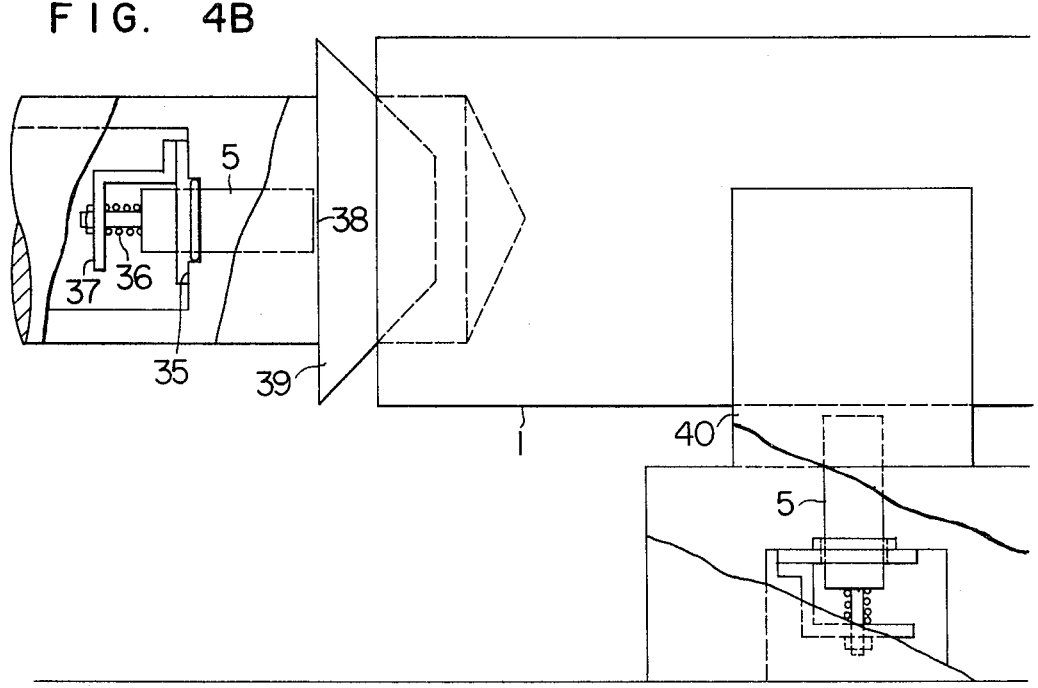
Figure 4A:
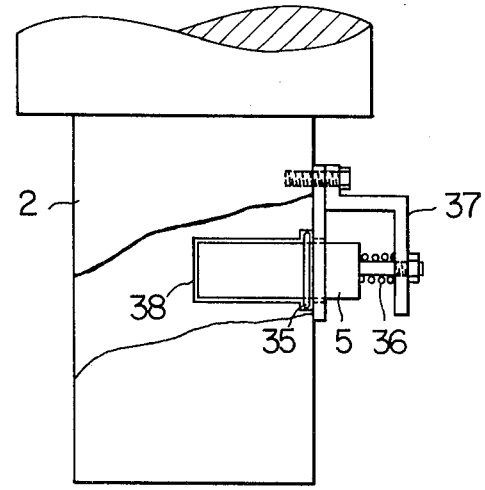

In FIG. 4B, the manners in which the sensor 5 is mounted on a work chuck part 39 or on a fixture 40 are illustrated. Same components as those shown in FIG. 4A are denoted by the same reference numerals, and any further description is omitted.

We claim:

1. A method of detecting cracks produced in a workpiece when the workpiece is processed so that the distortion thereof is mechanically removed comprising steps of:

setting a first period in which an acoustic emission signal is produced due to cracks possibly produced in the workpiece in the course of processing for mechanically removing the distortion and a second period in which an acoustic emission signal is produced due to causes other than said cracks;

determining occurrence or non-occurrence of said cracks by comparing an acoustic emission signal produced during said first period with a first predetermined value, said acoustic emission signal being contained in an output signal produced by an acoustic emission signal detecting sensor embedded in a portion of a distortion removing machine; and diagnosing whether or not the crack detecting system operates properly by comparing the acoustic emission signal produced during said second period with a second predetermined value.

2. An apparatus for detecting cracks produced in a workpiece when the workpiece is processed so that the distortion thereof is mechanically removed, which comprises:

a sensor receiving an acoustic emission signal from the workpiece and embedded in a particular portion of a distortion removing machine; and a detector circuit responsive to the output of said sensor to compare the output of said sensor with a first and second reference value, representative, respectively, of non-occurrence of cracking, and acoustic emission signals due to causes other than cracking of the workpiece, to provide a detection signal indicative of occurrence of the cracks when the output of said sensor exceeds both of said first and second reference values and the distortion removing machine exerts a pressure to the workpiece.

3. An apparatus according to claim 2 wherein said sensor is inserted in a hole formed in a pressing rod of the distortion removing machine and applied with a constant pressure from a spring supported by a sensor holder.

4. An apparatus according to claim 2 wherein said sensor is inserted in a hole formed in a support table of the distortion removing machine and applied with a constant pressure from a spring supported by a sensor holder.

5. An apparatus according to claim 2 wherein said detector circuit includes:

a first comparator comparing the output of said sensor with a first reference value to produce a first comparison signal when the sensor output exceeds the first reference value;

a second comparator comparing the output of said sensor with a second reference value to produce a second comparison signal when the sensor output exceeds the second reference value;

a limit switch operable to be closed during the time when said distortion removing machine continues to exert a pressure to the workpiece;

a first gate circuit passing the output of said first comparator when said limit switch is maintained to be closed;

a second gate circuit passing the output of said second comparator when said limit switch is maintained to be closed;

a first counter receiving the output pulse signal of said first comparator through said first gate circuit to provide a first count signal;

a second counter receiving the output pulse signal of said second comparator through said second gate circuit to provide a second count signal;

a third gate circuit passing the first count signal when said limit switch is maintained to be closed;

a fourth gate circuit passing the second count signal when said limit switch is maintained to be closed;

a first display responsive to the output of said third gate circuit to selectively display the absence of cracks and the failure of the detector itself; and a second display responsive to the output signal of said fourth gate circuit to display the occurrence of cracks.

* * * * *